United States Patent [19]

Yanuck, Jr.

[11] Patent Number: 4,753,227
[45] Date of Patent: Jun. 28, 1988

[54] ERECTION DEVICE AND METHOD
[76] Inventor: Rudolph R. Yanuck, Jr., 901 Charles St., Mechanicsburg, Pa. 17055
[21] Appl. No.: 64,551
[22] Filed: Jun. 22, 1987
[51] Int. Cl.⁴ .............................................. A61F 5/41
[52] U.S. Cl. .................................................... 128/79
[58] Field of Search ..................... 128/79, 303 A, 326

[56] References Cited
U.S. PATENT DOCUMENTS

| | | | |
|---|---|---|---|
| 2,874,698 | 2/1959 | Sell | 128/79 |
| 3,744,486 | 7/1973 | Wilson | 128/79 |
| 3,760,810 | 9/1973 | Van Hoorn | 128/326 |
| 4,374,523 | 2/1983 | Yoon | 128/326 |
| 4,378,008 | 3/1983 | Osbon, Sr. | 128/79 |
| 4,628,915 | 12/1986 | Chaney | 128/79 |

OTHER PUBLICATIONS

Nadig, Perry W., et al., "Noninvasive Device to Produce and Maintain an Erection-Like State", *Urology*, Feb. 1986, pp. 126-131.
User Information pamphlet for the Vacume Constriction Device sold by KSI, Inc. of West Chester, Pa. 19382.

*Primary Examiner*—Gene Mancene
*Assistant Examiner*—Cary E. Stone
*Attorney, Agent, or Firm*—Gerald Post

[57] ABSTRACT

A device for inducing and maintaining an erection of the male genital organ comprising a tubular member that is open at one end and receptive of the organ. A pump is affixed to the tube and, upon activation, withdraws air from the tube causing blood to flow into the inserted organ thereby enlarging and rigidizing it. When the organ has attained the desired erection, the pump is stopped and an elastic constriction band is disposed over the base of the organ. The band prevents the return flow of blood from the organ thereby capturing the erection. Simultaneous with the application of the band, a valve is allowed to open permitting outside air to enter the tube and equalize the pressure to make it easier to remove the device from about the erected organ.

16 Claims, 2 Drawing Sheets

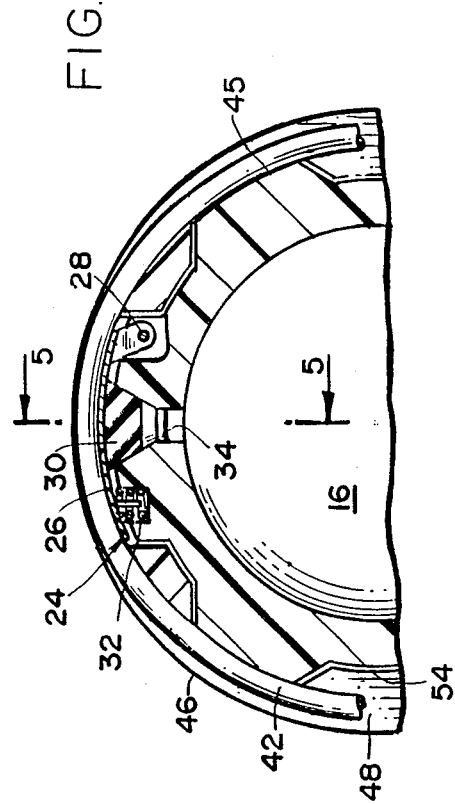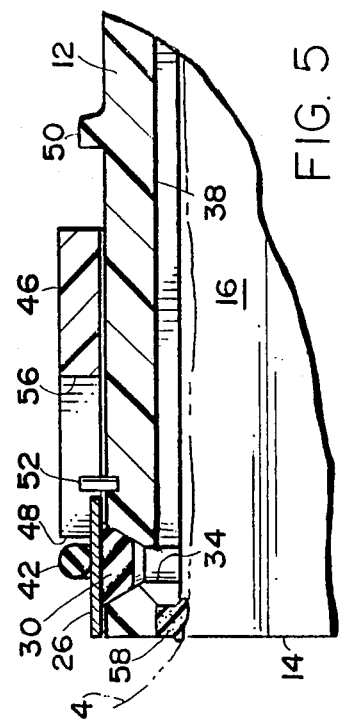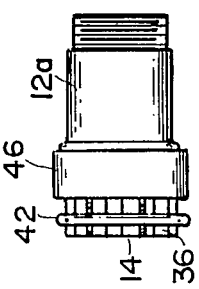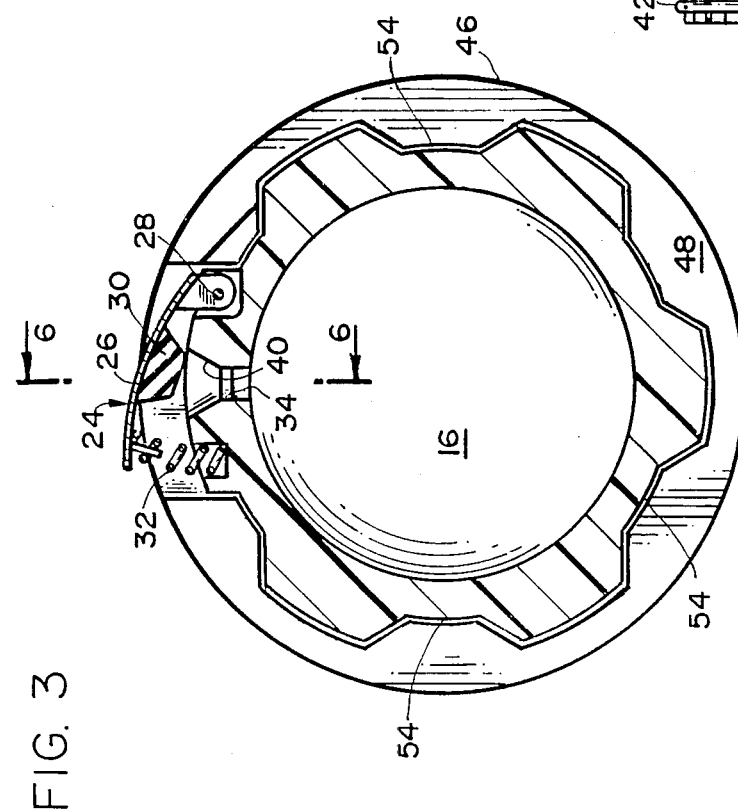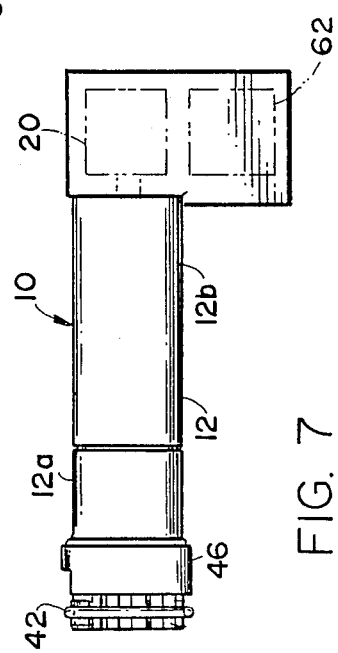

ERECTION DEVICE AND METHOD

BACKGROUND OF THE INVENTION

1. Field of the Invention

The invention is directed to the field of devices that aid in obtaining and maintaining an erection of the male genital organ.

2. Description of the Prior Art:

Male impotence is a problem faced by many men giving rise to sociological and psychological problems affecting both the man and his partner.

Devices have been developed to cause the erection of the human penis by inducing blood to flow into the organ. An article published in "Urology" of February, 1986 by Nadig, et al testifies to the efficiency and desirabliity of such devices. These devices, which are disclosed in U.S. Pat. Nos. 2,874,698 to Sell, 3,744,486 to Wilson and 4,378,008 to Osbon, all comprise a tubular member that is configured to accept the male organ. A similar device offered for sale by KSI, Inc. of West Chester, PA comprises the same features as the referenced U.S. Patents. They further include a vacuum pump or other means for evacuating the tube causing the blood to flow into the inserted penis to obtain engorgement and rigidity whenever desired by the user. When the penis has been sufficiently enlarged to the proper size, an elastic constriction band is positioned about the base of the erection. In order to facilitate the removal of the tubular member, atmospheric pressure must be restored therein. This is accomplished by opening a valve that puts the inside of the tube in fluid communication with the outside air.

However, all of the above cited devices are not completely satisfactory in performing these operations in that they require separate and distinct operations for applying the elastic constriction band and for opening the valve. The user of one of these devices has the inconvenience and distraction of seeking out and manipulating a valve prior to removal of the device and the commencement of normal copulation. Another deficiency of some of these devices is that extraneous skin of the scrotum is often drawn into the chamber by the vacuum if the device is carelessly applied.

SUMMARY OF THE INVENTION

The present invention overcomes the limitations of the prior art. The principle object of this invention is to provide a device that will easily aid in the formation of a penile erection, prevent extraneous skin of the scrotum from being drawn into the chamber by the vacuum, provide means for applying the elastic constriction band for retention of the erection and then be quickly and easily separable from the organ by causing the retention and separation functions to occur simultaneously.

A further object is to provide a vacuum pump that can be manually or elastically actuated to evacuate the tube.

A still further object is to provide a device that can be separated into sections to make a more compact unit and facilitate the cleaning of the tube.

A still further object is to provide a resilient cushioning material such as sponge rubber around the entrance of the tube to prevent skin from the scrotum from being drawn into the tubes when it is evacuated and to increase the comfort to the user.

A still further object is to provide a device that is complete and portable requiring no external source of electrical energy to actuate the pump.

A still further object is to provide a device that would be utilized to maintain a naturally occurring erection by those men suffering from organic impotence and tend to quickly lose the erection.

These and other objects are achieved by the preferred embodiment of the present invention which comprises a tubular member that has an opening at one end receptive of the faccid penis. At the other end of the tube, there is affixed an air vacuum pump that may be manually or electrically actuated. Upon activation of the pump, the chamber is evacuated reducing the air pressure surrounding the penis. The effect of this lowered pressure causes blood to flow rapidly into the penis causing it to become enlarged and rigid.

In order to prevent the blood from flowing out of the penis, an elastic constriction band is then placed about the base of the organ to constrict the vessels and preclude the reverse flow of blood.

The elastic constriction band will remain in place throughout intercourse, however, the air pressure within and without the device must be equalized to facilitate removal of the device. The present invention allows for equalizing this pressure simultaneously with the deployment of the elastic constriction band permitting immediate removal of the device and eliminate fumbling with the device when the man and his partner are mentally and physically prepared for intercourse.

Having in mind the above the other objects that will be obvious from an understanding of the disclosure, the present invention comprises a combination and arrangement of parts illustrated to the presently preferred embodiments of the invention which are hereinafter set forth in sufficient detail to enable those persons skilled in the art to clearly understand the function, operation, construction and advantage of it when read in conjunction with the accompanying drawings.

BRIEF DESCRIPTION OF THE DRAWINGS

The invention will be described in detail, by way of example, with reference to the accompanying drawings in which:

FIG. 3 is a sectional view taken along line 3—3 in FIG 2 showing the device with the valve actuated to an open position;

FIG. 4 is a sectional view taken along line 4—4 in FIG 2 showing the device with the valve actuated to a closed position by the elastic constriction band;

FIG. 5 is a partial sectional view taken along line 5—5 in FIG. 4;

FIG. 6 is a partial sectional view taken along line 6—6 in FIG. 3;

FIG. 7 is an orthographic view of the complete device; and

FIG. 8 is an orthographic view of a device for maintaining an erection.

DESCRIPTION OF THE PREFERRED EMBODIMENT

Figure 1:
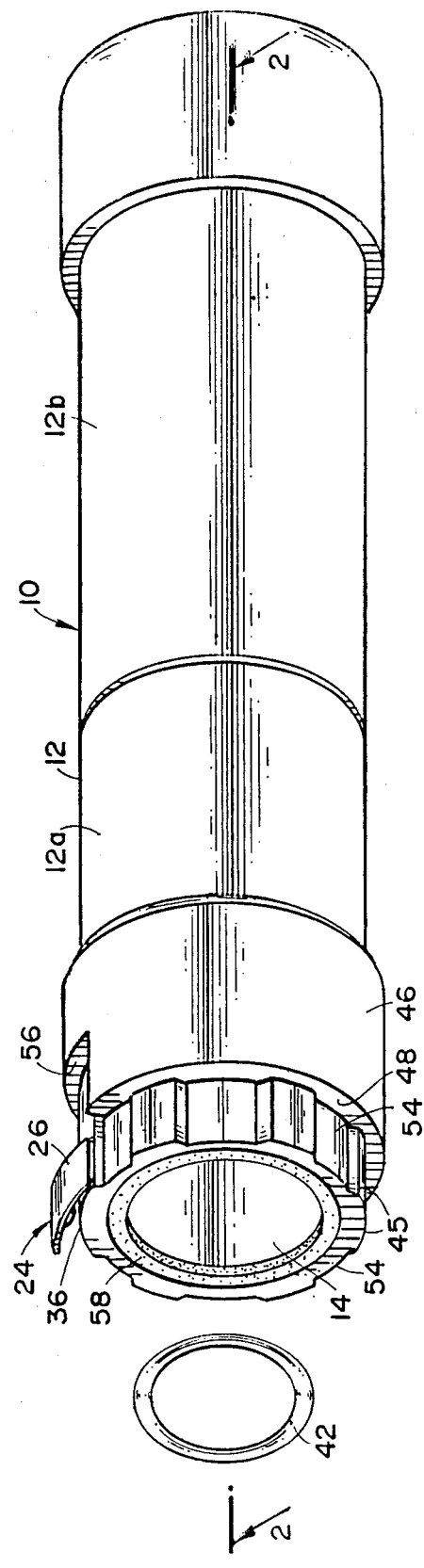
FIG. 1 is a pictorial view of the device.
Figure 2:
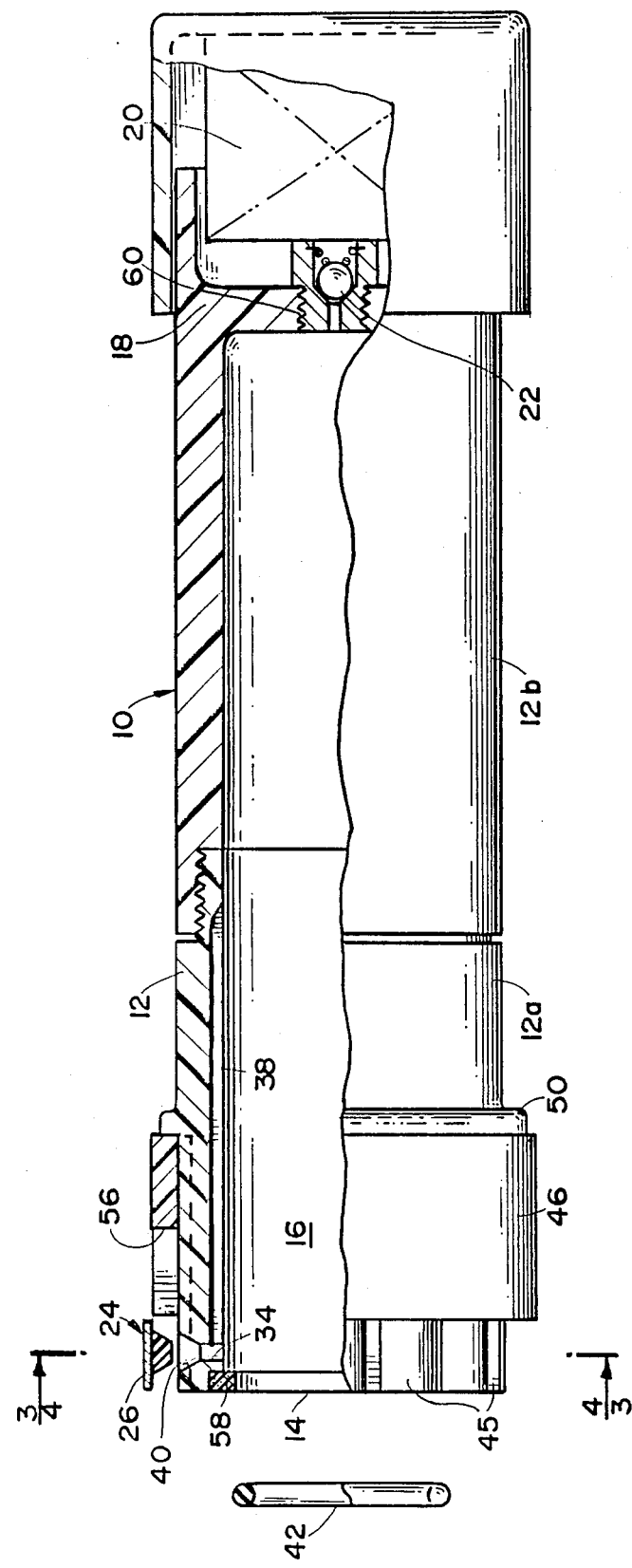
FIG. 2 is a partial sectional view taken along line 2—2 in FIG. 1.

Referring to FIGS. 1 and 2 of the drawings and in accordance with the principles of the invention, a device 10 for inducing an erection of the male genital organ is shown. The device 10 comprises an elongated tubular member 12 that has an opening 14 at one end. The volume within the tubular member 12 defines a chamber 16 receptive of the flaccid penis. The other end 18 of the tube 12 has connected thereto means for evacuating the chamber 16 such as an electrically actuated, positive displacement air pump 20. The pump 20 cooperates with a one-way valve 22 disposed within a threaded housing 60 releasably connected to the tubular member 12 to allow air to be withdrawn from the chamber 16 whenever the pump 20 is actuated. A pressure relief valve (not shown) can be installed to limit the vacuum pressure created in the chamber 16. The pump 20, one-way valve 22 and relief valve are well known in the art and are not described in detail.

The chamber 16 is designed to be evacuated after insertion of the flaccid penis since the reduced pressure therearound will compel blood to enter the organ engorging and ridigizing it to produce the erection. Once the erection has been attained, the pressure in the chamber 16 is allowed to return to atmospheric pressure to facilitate removal of the device 10. Valve means shown in FIGS. 2-6 comprises a valve assembly 24 that includes a valve sealing arm 26 pivotally connected by pin 28 to the tubular member 12 and is actuatable from a closed position wherein the chamber 16 is sealed from the atmosphere to an open position wherein the chamber is in fluid communication with the atmosphere. The arm 26 has affixed to it a tapered plug 30 of resilient material such as rubber and a biasing spring 32 for urging the valve arm 26 to the open position. The value means further includes means defining an aperture 34 passing through a wall portion 36 of the tubular member putting the chamber 16 in fluid communication with the outside atmosphere. The aperture 34 joins with an elongated groove 38 formed into the inner surface of the tubular member 12 to preclude the possibility of the erected organ blocking exposure of the chamber 16 to the outside air when the valve assembly 24 is actuated to the open position. The wall portion 36 is countersunk to give the aperture 34 a taper 40 matching that of the plug 30. The valve assembly 24 and the aperture 34 are so disposed that when the arm 26 is actuated to the closed position, the tapered plug 30 aligns with and bears against the tapered portion 40 of the aperture 34 effectively sealing the chamber 16 by eliminating fluid communication through the aperture.

Simultaneous with the opening of the valve assembly 24, the erection, once attained, is maintained by the application of an elastic constriction band 42 about the base of the erected organ 44. The means for moving the received elastic band 42 from a mounting surface 45 on the tubular member where it had been mounted or stretched over prior to using the device 10 comprises a sleeve 46 having a forward surface 48 and is axially slidable over the tubular member 12, including the mounting surface 45. The sleeve 46 is movable from a first position disposed between the valve assembly 24 and the other end 18 as shown in FIG. 2 defining the extent of the mounting surface 45 and against a stop flange 50 where it is held thereagainst by a detent (not shown), and a second position, as shown in FIG. 6 wherein the forward surface 48 is in edge alignment with the open end 14. A removable stop pin 52 retains the sleeve 46 on the tubular member 12.

The valve assembly 24 when actuated to the closed position overlays a section of the mounting surface 45 and is in turn overlayed by the mounted elastic band 42 thereby retaining the valve assembly in the closed position. The band 42 is moved off the tubular member 12 in response to the movement the sleeve 46 from the first position to a point where the forward surface 48 contacts the band 42 (FIG. 5) and continues moving until it achieves the second position (FIG. 6) where the band 42 is forced off the mounting surface 45 and disposes itself about the base of the erected organ 44. The elasticity of the band 42 is such that the radial compressive force against the organ 44 is sufficient to prevent the return flow of blood thereby maintaining the erection. The displacement of the band 42 allows the spring 32 to actuate the valve arm 26 to the open position where the plug 30 is spaced apart from the aperture 34 admitting air into the chamber 16 to allow the equalization of presure within and without the chamber.

To assure smooth movement of the band 42, the mounting surface 45 for mounting the band includes a plurality of longitudinally disposed and spaced apart means defining notches 54. The inner surface of the sleeve 46 is configured to conform with the notched mounting surface 45 to guide the movement of the band 42 since a portion of its forward surface 48 will lie beneath the inner circumference of the band 42. The sleeve 46 also includes a cut-out 56 in the forward surface 48 to allow free movement of valve assembly 24.

A soft resilient ring 58 made of foam rubber or plastic is affixed to the inner diameter of the tubular member 12 at the open end 14 the purpose of which is to form a tight seal against the inserted penis and to prevent skin from the scrotum from being drawn into the chamber 16 when it is evacuated.

The tubular member 12 is made of at least two threadedly connected sections 12a, 12b. The forward section 12a contains the opening 14 while the rear section 12b is able to accept the vacuum pump 20. The advantages of having the tubular member 12 as a two or more part assembly are to make the device 10 more compact when disassembled, to allow for easy cleaning of the inside of the cylinder 14 after use, and to be able to replace either tubular member with others of differing inner diameters and/or lengths for those men who have larger or smaller penises.

In dimensions, the diameter of the chamber 14 should preferably be 1¾" to 2-0" (44.5 to 50.8 millimeters) and have a total length of 8" (203 m.m.). However, since some males have organs significantly larger than average, the forward section 12a can be replaced to increase the total length and diameter. While the forward section would normally be approximately 3" (76 m.m.) long an enlarged portion would measure 5" (127 m.m.). The rear section is 5" (127 m.m.) long and would also be available in alternative diameters.

In use, one first positions the elastic constriction band 42 over the mounting portion 45 of the tubular member 12 and of the valve arm 26 while the valve assembly 24 is actuated to the closed position as shown in FIGS. 5 and 6. The flaccid penis which has been lubricated with mineral oil or the like, is inserted through the front opening 14 and into the chamber 16. The front surface of the tubular member 12 is pressed against the body about the base of the penis to establish an air tight seal thereat. The pump 20 is then activated either manually or electrically in order to evacuate the chamber thereby inducing blood to flow into the penis causing it to engorge and become erect and rigid. When electrically actuated, the pump 20 is powered by a battery 62 disposed within the device 10 as shown in FIG. 7. The sleeve 46, which had been retained against the stop flange 50 is then pulled forward dislodging the elastic constriction band 42 from the mounting surface 45 of the tubular member 12 and from the valve arm 26 to a position over the base of the erected penis 44. The elastic band 42 compresses the penis at its base with sufficient force to prevent the return flow of blood and thereby capturing the erection. Simultaneous with the dislodging of the elastic constriction band 44, the valve assembly 24 actuates to the open position admitting outside air into the chamber 16 equalizing the pressure within and without to facilitate removal of the device 10. Copulation may then be accomplished and the penis will remain erect until the band 42 is removed allowing the return flow of blood.

There are some males who suffer from organ impotence but can, at times, achieve a natural erection. However, it is often of short duration. These individuals can make use of the instant invention to maintain the erection. FIG. 8 shows the forward section 12a of the tubular member including the sleeve 46 and the mounted elastic band 42. In this case, the user would insert the erected organ through the section 12a and dislodge the band 42 about the base of the organ to capture the erection.

While the preferred embodiments of the invention are described, it will be understood that the invention is in no way limited by these embodiments.

What is claimed is:

1. A device for inducing an erection of the male genital organ comprising:
   an elongated tubular member open at one end defining a chamber receptive of the flaccid organ;
   means connected to the other end of said tubular member for evacuating air from said chamber to induce the flow of blood into the inserted organ causing the erection of same;
   valve means affixed to said tubular member and actuatable from a closed position to an open position wherein said chamber is in fluid communication with the surrounding atmosphere; and
   means disposed on the tubular member receptive of an elastic band for moving a received band about the base of the inserted organ preventing the return flow of blood from the organ in order to maintain the erection while simultaneously actuating said valve means from the closed position to the open position thereby equalizing the air pressure within and without said chamber to facilitate the removal of the device from the organ.

2. The device as recited in claim 1, wherein said valve means includes means defining an aperture through a wall of said tubular member for providing a fluid passage from said chamber to the atmosphere and further includes a valve sealing arm pivotally mounted on said tubular member wherein said arm superposes the aperture in the closed position and wherein said arm is biasedly urged to the open position disposing same apart from the aperture.

3. The device as recited in claim 2, wherein the means for moving the elastic band includes
   a sleeve axially slidable mounted over said tubular member and movable from a first position intermediate of the valve means and the other end of the tubular member to a second position in edge alignment with the open end, and further includes
   a mounting surface for the elastic band about the tubular member disposed between the open end and the first position of said sleeve wherein the received elastic band overlays said valve sealing arm retaining same in the closed position.

4. The device as recited in claim 3, wherein said tubular member comprises at least two releasably connected sections and wherein the air evacuating means is releasably connected to one of said sections.

5. The device as recited in claim 4, wherein the means for evacuating air includes a positive displacement air pump cooperating with a one-way valve to selectively permit a quantity of air to be expelled from said chamber upon actuation of said pump.

6. The device as recited in claim 5, wherein said air pump is electrically actuated.

7. The device as recited in claim 6, wherein the source of electrical energy comprises a battery mounted within the device.

8. The device as recited in claim 1, further including a ring of resilient material affixed to the inner surface of the tubular member at the open end thereof.

9. A device for inducing and maintaining an erection of the male genital organ comprising:
   an elongated tubular member open at one end defining a chamber therein for insertion of the flaccid organ;
   means connected to the other end of said tubular member for evacuating said chamber while the open end is pressed against the body to seal the open end thereby inducing the flow of blood into the organ causing the erection of same;
   valve means affixed to said tubular member, said means actuatable from a closed position to an open position wherein said chamber is in fluid communication with the surrounding atmosphere;
   an elastic band configured to provide an axially compressive force sufficient to restrict the return flow of blood from the organ when disposed about the base thereof;
   means disposed on the tubular member receptive of an elastic band for moving a received band about the base of the inserted and erected organ to prevent the return flow of blood therefrom for maintaining the erection while simultaneously actuating said valve means from the closed position to the open position thereby equalizing the air pressure within and without said chamber to facilitate removal of the device from the organ.

10. The device as recited in claim 9, wherein said valve means includes means defining an aperture disposed through the tubular member for exposing said chamber to the atmosphere and further includes a valve sealing arm pivotally mounted on the tubular member wherein said arm superposes the aperture in the closed position to seal same and where said arm is biasedly urged to the open position disposing same apart from the aperture.

11. The device as recited in claim 10, wherein the means for moving the elastic band includes a sleeve axially slidably mounted over said tubular member and movable from a first position intermediate of the valve means and the other end of the tubular member to a second position wherein said sleeve is in edge alignment with the open end, and further includes a mounting surface for the elastic band disposed on the tubular member between the open end and the first position of said sleeve and wherein the received elastic band overlays said valve sealing arm retaining same in the closed position.

12. The device as recited in claim 11, wherein said mounting surface for the elastic band includes means defining a plurality of longitudinally disposed spaced apart notches, and wherein the inner surface of said sleeve is configured to conform to said mounting surface to facilitate the movement of the band in response to the movement of said sleeve from the first position to the second position.

13. The device as recited in claim 12, wherein said tubular member comprises at least two releasably connected longitudinal sections and wherein the air evacuating means is releasably connected to one of said sections.

14. A method for inducing an erection of the male genital organ comprising the steps of:
providing a tubular member open at one end defining a chamber for receiving the organ, said tubular member having connected to the other end thereof means for evacuating air from said chamber and including valve means affixed to said tubular member actuatable from a closed position to an open position wherein said chamber is in fluid communication with the atmosphere and further including means disposed on the tubular member receptive of an elastic band for moving a received band about the base of the organ;
applying an elastic band over the tubular member to the receptive means wherein said received band also actuates said valve means to the closed position;
inserting the flaccid organ into the chamber and pressing the open end of the tubular member thereby sealing said chamber from the atmosphere;
evacuating the air from said chamber to induce the flow of blood into the organ and causing the erection thereof;
dislodging the elastic band from the tubular member to a position about the base of the organ for preventing the return flow of blood therefrom thereby maintaining the erection wherein the dislodgement of said band simultaneously actuates said valve means to the open position thereby releasing the pressure within and without the device to facilitate the removal thereof.

15. The method as recited in claim 14, wherein the step of providing valve means further includes providing means defining an aperture disposed through the tubular member exposing said chamber to the atmosphere and further includes a valve sealing arm pivotally mounted on the tubular member wherein said arm superposes the aperture in the closed position to seal same and where said arm is biasedly urged to the open position disposing same apart from the aperture.

16. The method as recited in claim 15, wherein the step of providing means for moving an elastic band includes providing a sleeve axially slidably mounted over the tubular member and movable from a first position intermediate of the aperture and the other end of the tubular member to a second position wherein said sleeve is in edge alignment with the open end, and further includes a mounting surface for the elastic band disposed on the tubular member between the open end and the first position of said sleeve and wherein the received elastic band overlays said valve sealing arm retaining same in the closed position.

* * * * *